US005626142A

United States Patent [19]
Marks

[11] Patent Number: 5,626,142
[45] Date of Patent: May 6, 1997

[54] MULTIPLE CUFF BLOOD PRESSURE SYSTEM

[76] Inventor: Lloyd A. Marks, 1021 Minisink Way, Westfield, N.J. 07090

[21] Appl. No.: 435,158

[22] Filed: May 5, 1995

[51] Int. Cl.⁶ ........................................................ A61B 5/00
[52] U.S. Cl. .......................... 128/686; 128/677; 128/679; 606/202
[58] Field of Search .................... 128/677–683, 128/686, 687; 606/202

[56] References Cited

U.S. PATENT DOCUMENTS

| | | |
|---|---|---|
| 2,193,945 | 3/1940 | Strauss et al. . |
| 3,699,945 | 10/1972 | Hanafin ............................ 128/686 |
| 4,210,154 | 7/1980 | Klein ................................ 128/686 |
| 4,321,929 | 3/1982 | Lemelson et al. . |
| 4,479,494 | 10/1984 | McEwen . |
| 4,651,748 | 3/1987 | Vinogradov et al. . |
| 4,718,428 | 1/1988 | Russell . |
| 4,800,892 | 1/1989 | Perry et al. ........................ 128/679 |
| 5,003,981 | 4/1991 | Kankkunen et al. ............. 128/687 |
| 5,022,403 | 6/1991 | LaViola . |
| 5,240,008 | 8/1993 | Newell ............................... 128/677 |
| 5,243,991 | 9/1993 | Marks . |
| 5,447,160 | 9/1995 | Kankkunen et al. ............. 128/686 |
| 5,464,019 | 11/1995 | Anderson et al. ................ 128/677 |

*Primary Examiner*—Angela D. Sykes
*Assistant Examiner*—Robert Nasser
*Attorney, Agent, or Firm*—Wigman, Cohen, Leitner & Myers, P.C.

[57] ABSTRACT

A multiple blood pressure cuff system comprises a plurality of inflatable cuffs of a range of widths and lengths which collectively share a common pressure source and a common pressure measuring device. A manifold pneumatically connects each cuff to the common pressure source and pressure measuring device and stopcock valves allow airflow to be directed to only the particular cuff in use. A mounting board is provided for affixing the system to a wall or cabinet and for conveniently supporting and displaying the cuffs that are not in use.

28 Claims, 2 Drawing Sheets

MULTIPLE CUFF BLOOD PRESSURE SYSTEM

FIELD OF THE INVENTION

The present invention relates to sphygmomanometers and more particularly to a system of multiple inflatable blood pressure cuffs for measuring systolic and diastolic arterial blood pressure values without resort to invasive techniques.

BACKGROUND OF THE INVENTION

The most common method for non-invasive arterial blood pressure measurement uses an inflatable cuff which circumscribes an extremity, typically an upper arm. Once attached, the air pressure within the cuff is increased to a value well in excess of typical systolic pressure. As the air is controllably released, blood pressure is estimated by detecting "Korotkoff" sounds using a stethoscope placed on the limb near the artery. Those sounds are produced by disturbances in the arterial blood flow due to partial occlusions of the artery caused by the externally applied cuff pressure. As the cuff pressure is reduced the systolic pressure equals the cuff pressure at the time the first Korotkoff sound is detected. The diastolic pressure is identified when silence occurs. Manual pressure readings for systolic and diastolic pressure are determined by noting the scale value in millimeters of the height of a mercury column, or the pointer on an aneroid pressure gauge, which is pneumatically connected to the cuff air pressure. Devices of this type are commonly referred to as "sphygmomanometers."

In order for the above-described sphygmomanometer to yield accurate diagnostic readings, the cuff must have a width appropriate to the circumference of the patient's limb to which the cuff is applied. Most cuffs in use today comprise an elongated inflatable bladder with VELCRO® hook and loop fastener sections at each end. In my prior U.S. Pat. No. 5,243,991, the disclosure of which is incorporated herein by reference, there is disclosed an adjustable blood pressure cuff and a method of measuring blood pressure. My prior cuff and method avoid the errors resulting from using a blood pressure cuff having an improper width in relation to the circumference of the limb of the patient whose blood pressure is to be measured. That is accomplished by providing a flexible bladder which is foldable upon and removably retained to itself by means of hook-and-loop fasteners, such as Velcro® fasteners, attached to both sides of the bladder. In this way, a cuff width, such as 0.4 times the circumference of the limb as recommended by the American Heart Association, can be set by folding over and removably securing the hook-and-loop fasteners to achieve the appropriate cuff width. Critical diagnostic errors may arise if a cuff of improper width is utilized.

In addition to the width requirement, the inflatable cuff should be of a length which allows it to completely circumscribe the extremity to which is it is being applied without excessive overlap. Preferably, the length of the inflatable bladder should be somewhat larger than the circumference of the limb to which it is to be applied. If the cuff is too short, it may be difficult to apply, or if applied could be so tight as to be uncomfortable to the patient or prevent Korotkoff sounds from being detected. If the cuff is too long for the particular limb circumference to which it is applied, it may be difficult to secure the cuff, and thus may render it difficult to obtain the requisite pressure needed to occlude the artery and measure the patient's blood pressure.

Because of the importance of using a properly fitted cuff to yield accurate blood pressure readings, the American Heart Association recommends that a number of different-sized cuffs be maintained and utilized by medical practitioners to accommodate the range of patient arm widths, from pediatric to large adult size. In particular, health care providers must typically maintain at least five different-sized blood pressure cuffs in each examination room to accommodate of the following patient populations: infant, pediatric, adult, and large adult, and an extra large cuff to circumscribe the thigh of a patient whose pressure is being measured at the femoral artery.

Maintaining five or more separate blood pressure units is both expensive and cumbersome, especially in a clinical setting where many rooms need to be equipped with a full set of cuffs. Conventionally, each blood pressure unit has its own inflation bulb and aneroid gauge, thereby adding to its expense. If use of a more accurate wall mounted mercury manometer is employed, the appropriate blood pressure unit must be mechanically coupled and uncoupled to the manometer which often leads to difficulty because of jamming, misplaced tools and missing cuffs. Furthermore, storing five or more complete cuffs can be disadvantageous, especially in cramped quarters, such as an ambulance, "medivac" helicopter, military field hospital or the like.

Accordingly, it would be desirable to provide a single blood pressure cuff system which has appropriately sized blood pressure cuffs that can be used to accurately measure the blood pressure of infants, children, adults, and large adults, at both the brachial and femoral arteries, in a manner which is convenient, economical, conserving of space, and not susceptible to the other disadvantages mentioned above.

SUMMARY OF THE INVENTION

The present invention is directed to a multiple blood pressure cuff system comprising a plurality of inflatable cuffs of a range of widths and lengths which collectively share a common inflation means and pressure measuring means. A manifold assembly pneumatically connects each cuff to the common inflation means and pressure measuring means with valve means, such as stopcock valves, which can be operated to limit airflow only to the particular cuff in use. A mounting board or plate is provided for mounting the system to a vertical surface, such as a wall or cabinet, and for conveniently supporting and displaying the cuffs for selection and use by medical practitioners.

A key advantage of the blood pressure system of the present invention is that it avoids the need for the practitioner to maintain five or more separate and complete blood pressure cuff devices for infant, pediatric and adult patients as well as for brachial and femoral applications. This is particularly economical since each cuff does not require its own separate inflation means and pressure measuring means, but is selectively connectable to a common inflation and pressure measuring means. The present invention conserves storage space which is especially advantageous if the device is employed in a cramped space, such as the cabin of an ambulance or medivac helicopter or a military field hospital. Additionally, because all of the different-sized cuffs are permanently connected to a single system, which in turn can be wall-mounted, the all-too-frequent problem of missing or misplaced tools, parts or cuffs is avoided. Furthermore, there is no incentive to temporarily remove a cuff for use since there is no inflation means or pressure measuring means associated with the individual cuffs.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
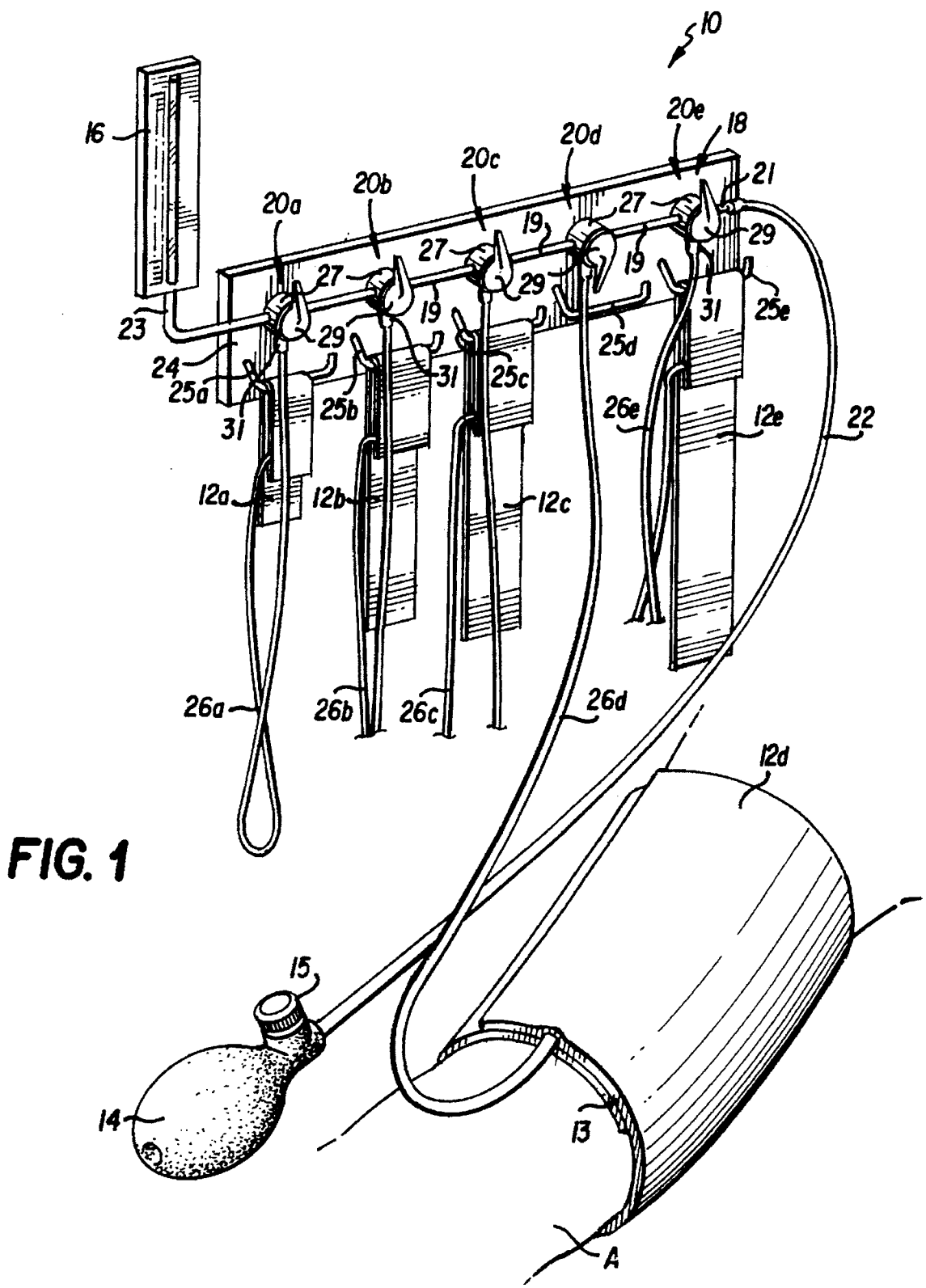
FIG. 1 is a perspective view of one embodiment of the multiple blood pressure cuff system of the present invention shown in use on a patient.

Referring now in detail to the drawings wherein like parts are designated by like reference numerals throughout, there is illustrated in FIG. 1 a perspective view of the multiple blood pressure cuff system of the present invention which is designated generally by reference numeral 10. Blood pressure system 10 generally comprises a plurality of inflatable cuffs 12a–12e of a range of widths and lengths which collectively share a common inflation means, such as pressure pump or bulb 14 and a common pressure measuring means, such as manometer 16. A manifold assembly 18 comprises a plurality of stopcock valves 20a–20e pneumatically connected to each other by pipe sections 19. As those skilled in the art will appreciate, the present invention is readily adapted for use with any automated method or apparatus for non-invasively measuring blood pressure with conventional blood pressure cuffs, such as the conventional oscillometric method.

At one end of the manifold assembly 18, a pipe section 21 connects the manifold to the inflation bulb 14 by means of a flexible tube 22. At the other end of manifold assembly 18, a pipe section 23 connects the manifold to the manometer 16. It is also possible to connect the manometer 16 to pipe section 21 or to any of the pipe sections 19 along the manifold assembly 18. The manifold assembly 18 is secured to a mounting board or plate 24 which is provided for mounting the system 10 to a vertical surface, such as a wall, cabinet or the like, and for conveniently supporting and displaying the cuffs that are not in use. For that purpose, a plurality of cuff hangers 25a–25e are affixed to the mounting plate 24 beneath the manifold assembly 18 and support the cuffs in the manner shown in FIG. 1.

Each of the cuffs 12a–12e may be of well known and conventional construction comprising an elongated inflatable bladder with strips or patches of a hook-and-loop type fastener, such as VELCRO® fastener, to allow the cuff to be secured firmly around the arm A (or leg not shown) of a patient as illustrated in FIG. 1. Alternative adjustable fastening means, such as straps, clips, etc., may also be employed. Preferably, at least five cuffs of varying sizes (width and length) are provided commensurate, for example, with the average arm circumference of patients in the categories of infant, pediatric, adult, and large adult, and an extra large size for circumscribing a patient's thigh for measuring blood pressure at the femoral artery.

Each of the cuffs 12a–12e is pneumatically connected to an outlet pipe 31 on a respective stopcock 20a–20e by means of flexible tubes 26a–26e. Such tubes are sufficiently long to be used at a distance from the manifold assembly 18, e.g., at an examination table or the like in an exam room. Each stopcock valve 20a–20e comprises a valve body 27 and an operator knob 29 with two positions. As shown in FIG. 1, the knob 29 associated with stopcock 20d and cuff 12d is positioned so as to permit air flow from bulb 14 through tube 22 into manifold assembly 18 via pipe 21, and thence to cuff 12d via flexible tube 26d. All the stopcocks 20a–20e are positioned to also permit air flow through the manifold assembly 18 and pipe 23 to manometer 16.

Figure 2:
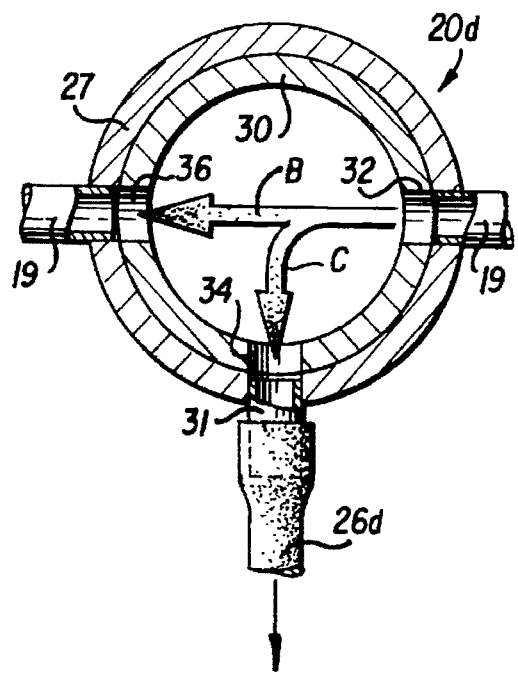
FIG. 2 is a cross-sectional view of a stopcock valve of the system of the present invention in an open position.
Figure 3:
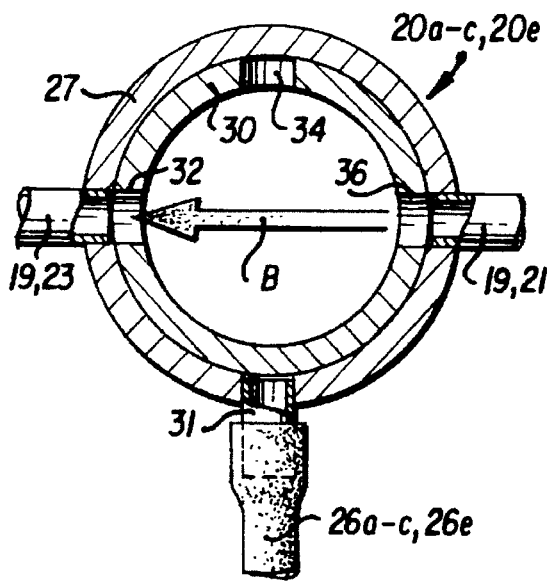
FIG. 3 is a cross-sectional view of the stopcock valve of FIG. 2 shown in a closed position.

Referring now to FIGS. 2 and 3, the construction of one possible embodiment of the stopcocks 20a–20e is illustrated to show how the stopcocks may be operated to permit use of only one of the cuffs 12a–12e. In the illustrated embodiment, the practitioner has selected cuff 12d as the appropriate cuff for the particular size of the limb of the patient whose blood pressure is to be measured.

FIG. 2 illustrates stopcock 20d which is in the "open" position so as to connect the pressure source (bulb 14) to the cuff 12d. Stopcock body 27 comprises an air tight chamber in which a cylindrical gate or plug 30 connected to a knob 29 is rotatably disposed. The gate 30 is provided with three ports 32, 34, 36 angularly spaced at 90° increments. With the gate positioned as shown in FIG. 2 (i.e., with the knob 29 on stopcock 20d oriented downwardly as shown in FIG. 1), ports 32 and 36 are aligned with pipe sections 19 so that air flows through stopcock 20d in the direction of arrow B. Port 34 is aligned with outlet pipe 31 so that air also flows in direction C through port 34, through outlet pipe 31 and flexible tube 26d and thence to cuff 12d.

FIG. 3 illustrates the positions of the stopcocks 20a–20c and 20e which are all in the "closed" position to connect the pressure source (bulb 14) to the manometer 16 and isolate or shut off air flow through outlet pipes 31 of stopcocks 20a–20c and 20e to cuffs 12a–12c and 12e. Air flows only in direction B through stopcocks 20a–20c and 20e.

The pressure source for the system 10 is disclosed as a conventional manual inflation bulb 14 having an air bleed valve 15. Alternatively, an electrically operated pneumatic pump may be employed. Manometer 16 is shown as a conventional mercury column, but alternatively may be an aneroid pressure gauge with a radial dial or an electronic pressure gauge. In addition, automated non-invasive blood pressure measuring means may be used, such as an oscillometric apparatus. Pneumatic tubing 22 and 26a–26e may be made of rubber or any suitable plastic tubing. Mounting board or plate 24 is preferably made of metal or plastic and is adapted to be mounted to a wall or cabinet by conventional mounting means (not shown). Indicia identifying the width of the cuff and/or the patient population for which it is intended may be provided adjacent to each hanger 25a–25e. It is contemplated that the present invention may be mounted to a wall in a clinical setting, i.e., an examination room, or inside the cabin of an ambulance or helicopter.

In use and operation, the medical practitioner selects the appropriate cuff 12a–12e based on the patient's limb size, etc. and opens only the stopcock valve associated with that particular cuff. All other valves are placed in the closed position. Blood pressure is then taken using the classic Korotkoff sound technique.

Figure 4:
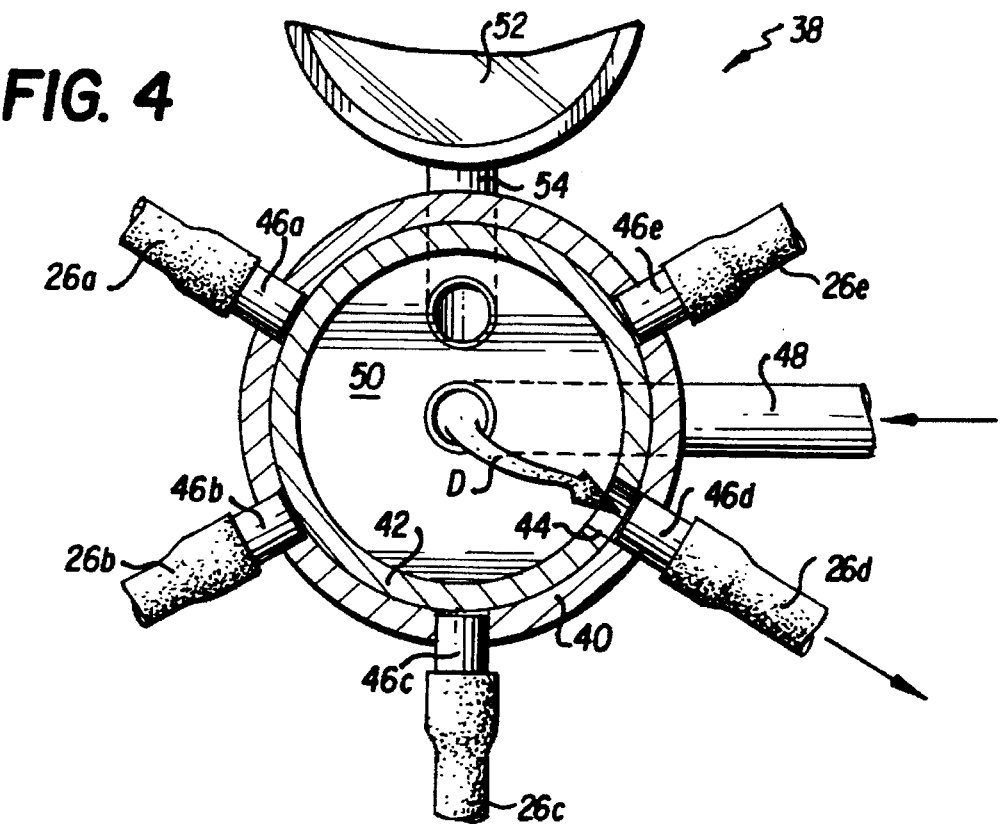
FIG. 4 is a cross-section view of an alternate embodiment of the manifold assembly for use with the present invention.

FIG. 4 illustrates an alternate embodiment of a manifold assembly 38 for use with the present invention. In this embodiment, the manifold assembly 38 comprises a five-position stopcock-type valve comprising a valve body 40 with a cylindrical gate or plug 42 that is adapted to be rotated about its central axis by means of a handle (not shown) similar to the knobs 29 of stopcocks 20a–20e of FIG. 1. Gate 42 is provided with a single port 44 in its periphery and valve body 40 has a plurality of radial pipe sections 46a–46e connected in bores in the cylindrical wall of body 40. An air inlet pipe 48 is connected centrally to valve body 40 so as to admit air flow as depicted by arrow D into the chamber 50 of cylindrical gate or plug 42 from an inflation means, such as a pressure pump or inflation bulb 14. A manometer or pressure gauge 52 is connected to the chamber 50 of gate or plug 42 by means of a pipe 54 so as to measure the air pressure in chamber 50.

Flexible tubes 26a–26e of the blood pressure cuffs 12a–12d shown in FIG. 1 are connected to a respective radial pipe 46. The gate or plug 42 may be rotated about its axis to align the port 44 with a selected pipe section 46a–46e and thereby connect the air pressure source via pipe 48 and pressure gauge 52 via pipe 54 to a respective blood pressure cuff 12a–12e via a respective flexible tube 26a–26e. In FIG. 4, cuff 12d has been connected via flexible tube 26d, pipe 46d and port 44 to chamber 50 so that air supplied via pipe 48 inflates cuff 12d and the air pressure therein can be measured by gauge 52.

The manifold assembly 38 may be mounted to a mounting plate similar to mounting plate 24. It will be appreciated that other forms of manifold assemblies and valve arrangements may be used to practice the present invention. Any such assemblies or arrangements that permit the flow of air to a selected one of a plurality of blood pressure cuffs are considered to be equivalent structures.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What I claim is:

1. A multiple cuff blood pressure system for measuring the blood pressure of different patients comprising:
   a fluid pressure source;
   at least three differently-sized inflatable cuffs from the group consisting of an infant cuff, a pediatric cuff, an adult cuff, a large adult cuff and a thigh cuff, each cuff being connected to said pressure source;
   means connected between said pressure source and said inflatable cuffs for directing fluid flow to a selected one of said inflatable cuffs; and
   means connected to said fluid pressure source for measuring fluid pressure in said selected inflatable cuff.

2. The system of claim 1, wherein said fluid pressure source is a manual inflation bulb and said pressure measuring means is one of a mercury manometer, an aneroid pressure gauge or an electronic pressure gauge.

3. The system of claim 1, wherein said inflatable cuffs comprise all of said infant cuff, pediatric cuff, adult cuff, large adult cuff, and thigh cuff.

4. The system of claim 1, wherein said inflatable cuffs each have a different width commensurate with the circumference of the limb of the patient whose blood pressure is to be measured.

5. The system of claim 1, wherein said flow directing means comprises a valve having a fluid inlet and a plurality of fluid outlets each connected to a respective inflatable cuff, gate means in said valve for connecting the fluid inlet in fluid flow communication with a respective one of said fluid outlets.

6. The system of claim 5, wherein said pressure measuring means is connected to said valve.

7. The system of claim 1, wherein said fluid pressure means comprises only one pressure measuring element.

8. A multiple cuff blood pressure system for measuring the blood pressure of different patients comprising:
   a fluid pressure source;
   at least two differently-sized inflatable cuffs from the group consisting of an infant cuff, a pediatric cuff, an adult cuff, a large adult cuff and a thigh cuff, each cuff being connected to said pressure source;
   means connected between said pressure source and said inflatable cuffs for directing fluid flow to a selected one of said inflatable cuffs; and
   means connected to said fluid pressure source for measuring fluid pressure in said selected inflatable cuff, said flow directing means comprising a manifold including a plurality of valves connected in series, each of said inflatable cuffs being connected to a respective one of said valves, said fluid pressure source and said pressure measuring means being connected to said manifold.

9. The system of claim 8, wherein said valves comprise stopcocks each having an open position in which fluid pressure flows through said stopcock and to the inflatable cuff connected thereto and a closed position in which fluid flows through said stopcock with flow interrupted to the inflatable cuff connected thereto.

10. The system of claim 8, wherein each of said inflatable cuffs is connected to its respective valve by an elongated flexible tube.

11. The system of claim 8, wherein said manifold comprises a plurality of first pipe sections connecting said valves in series, a second pipe section connecting said fluid pressure source to one of said valves at one end of said manifold and a third pipe section connecting said pressure measuring means to the other end of said manifold.

12. A multiple cuff blood pressure system for measuring the blood pressure of different patients comprising:
   a fluid pressure source;
   at least two differently-sized inflatable cuffs from the group consisting of an infant cuff, a pediatric cuff, an adult cuff, a large adult cuff and a thigh cuff, each cuff being connected to said pressure source;
   means connected between said pressure source and said inflatable cuffs for directing fluid flow to a selected one of said inflatable cuffs, said flow directing means comprising a manifold assembly supported on a mounting plate adapted to be secured to a vertical surface, said mounting plate having a plurality of hangers, each of said hangers supporting a respective one of said inflatable cuffs; and
   means connected to said fluid pressure source for measuring fluid pressure in said selected inflatable cuff.

13. A multiple cuff blood pressure system comprising:
   a manifold assembly comprising a plurality of fluid pressure valves connected in series;
   a pressure source connected to said manifold assembly and a pressure measuring device connected to said manifold assembly;
   a plurality of inflatable blood pressure cuffs each connected to a respective one of said valves, said valves being selectively operable to connect said pressure source and said pressure measuring device to only one of said inflatable cuffs.

14. The system of claim 13, wherein said valves are stopcocks.

15. The system of claim 14, wherein each of said stopcocks has an open position in which fluid pressure flows through said stopcock and to the inflatable cuff connected thereto and a closed position in which fluid flows through said stopcock with flow interrupted to the inflatable cuff connected thereto.

16. The system of claim 13, wherein said inflatable cuffs each have a different width.

17. The system of claim 13, wherein said manifold assembly is secured to a mounting plate, said inflatable cuffs being connected to said valves by elongated flexible tubes, said mounting plate having a plurality of hangers for supporting said inflatable cuffs when said cuffs are not in use.

18. The system of claim 13, wherein said pressure source is a manual inflation bulb and said pressure measuring device is one of a mercury manometer, aneroid pressure gauge or an electronic pressure gauge.

19. The system of claim 13, wherein said manifold assembly has a first end and a second end, said pressure source being connected to said first end and said pressure measuring device being connected to said second end.

20. The system of claim 13, wherein said pressure source and said pressure measuring device have a common connection to said manifold assembly.

21. A multiple cuff blood pressure system for measuring the blood pressure of different patients comprising:

a fluid pressure source;

at least three differently-sized inflatable cuffs for measuring the blood pressure of patients with different size arms, all said cuffs being connected to said pressure source;

valve means connected between said pressure source and said inflatable cuffs for directing fluid flow to a selected one of said inflatable cuffs; and means connected to said fluid pressure source for measuring fluid pressure in said selected inflatable cuff.

22. The system of claim 21, wherein said inflatable cuffs comprise an infant cuff, a pediatric cuff, an adult cuff, a large adult cuff, and a thigh cuff.

23. The system of claim 21, wherein said fluid pressure means comprises only one pressure measuring element.

24. A multiple cuff blood pressure system comprising:

a fluid pressure source;

a plurality of differently-sized inflatable cuffs, each being connected to said pressure source;

a manifold connected to said pressure source for directing fluid flow to a selected one of said inflatable cuffs, said manifold including a plurality of valves connected in series, each of said inflatable cuffs being connected to a respective one of said valves; and means connected to said manifold for measuring fluid pressure in said selected inflatable cuff.

25. The system of claim 24, wherein said fluid pressure source is a manual inflation bulb and said pressure measuring means is one of a mercury manometer, an aneroid pressure gauge or an electronic pressure gauge.

26. The system of claim 24, wherein said inflatable cuffs comprise an infant cuff, a pediatric cuff, an adult cuff, a large adult cuff, and a thigh cuff.

27. The system of claim 24, including a plurality of hangers, each hanger supporting a respective one of said inflatable cuffs.

28. The system of claim 24, wherein said manifold comprises a plurality of first pipe sections connecting said valves in series, a second pipe section connecting said fluid pressure source to one of said valves at one end of said manifold and a third pipe section connecting said pressure measuring means to the other end of said manifold.

* * * * *